Figure 1:
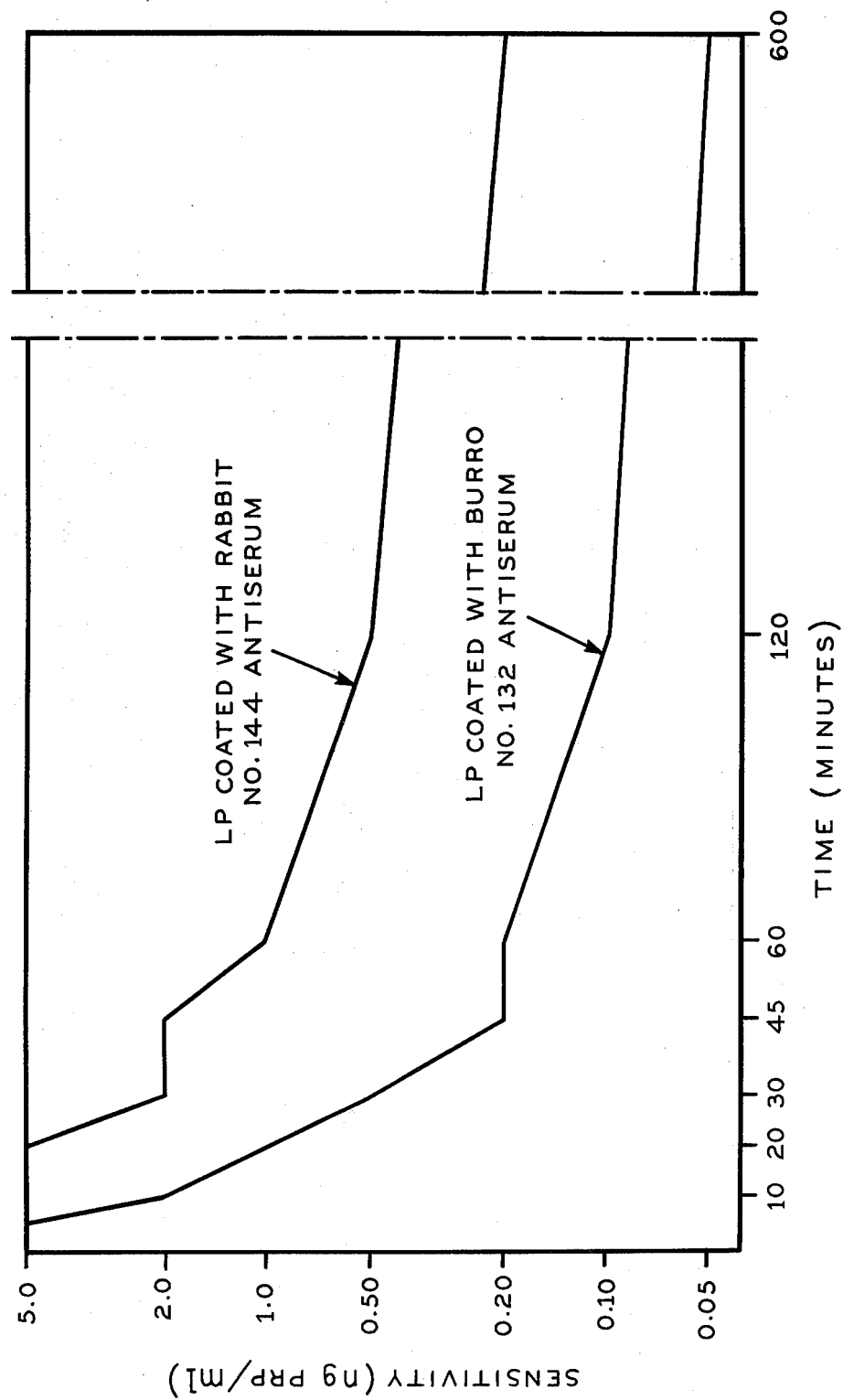

United States Patent [19]

Siber

[11] 4,310,508
[45] Jan. 12, 1982

[54] DIAGNOSTIC TEST AND REAGENT THEREFOR

[76] Inventor: George R. Siber, 37 Corey Rd., Brookline, Mass. 02146

[21] Appl. No.: 50,269

[22] Filed: Jun. 19, 1979

[51] Int. Cl.³ .................. G01N 1/28; G01N 33/48; G01N 33/54
[52] U.S. Cl. .................. 424/12; 23/230 B; 424/8; 424/11; 424/13; 424/78; 424/85; 424/86; 424/87; 424/88; 424/89; 424/92
[58] Field of Search ............ 424/8, 11, 12, 13, 78, 424/85–89, 92; 23/230 B

[56] References Cited

U.S. PATENT DOCUMENTS

| | | | |
|---|---|---|---|
| 3,600,494 | 8/1971 | Tomizawa | 424/13 |
| 3,873,683 | 3/1975 | Fishbein | 424/12 |
| 3,992,517 | 11/1976 | Lowke | 424/89 X |
| 4,157,383 | 6/1979 | Sedlacek | 424/12 X |

OTHER PUBLICATIONS

Boyd, Fundamentals of Immunology, Intersci Pub. N.Y. 3rd Ed. 1956, pp. 357–360, 369, 370.
DiPerri Chem. Abs. vol. 73, 1970, Ab. No. 12896s.
Maruyama, Chem. Abs., vol. 74, 1971 Ab. No. 11827d.
Merck & Co., Merck Index, Rahway, N.J. 7th Ed. 1960, p. 611.
Friedman et al. (Ed) Immunoserology in The Diagnosis of Infectious Dis., University Park Press Baltimore, Symp. Proceed–9th Annual ASM Eastern PaBr, Nov. 1977, Pub. 1979, pp. 25–31, 143–147.
Newman et al., J. of Lab. & Clin. Med., vol. 76, 1970, pp. 107–113.
Kabat, Structural Concepts in Immuno. & Immunochem. Holt, Rinehart & Winston, N.Y. 2nd Ed. 1976, pp. 238–258, 267–269.
Fritz, The J. of Immunol., vol. 108, 1972, pp. 108–111.

*Primary Examiner*—Anna P. Fagelson
*Attorney, Agent, or Firm*—Kevin B. Clarke

[57] ABSTRACT

A highly sensitive direct particle agglutination test capable of routinely detecting as little as 0.2 nanograms of antigen per milliliter of clinical fluid and characterized by uniform sensitivity as well as stability is disclosed as well as coated particles having a sensitivity of 0.2 nanograms antigen per milliliter and methods for preparing such coated particles. In addition, a method to reduce the frequency of non-specific agglutination with human sera to 2% or less is described.

14 Claims, 1 Drawing Figure

DIAGNOSTIC TEST AND REAGENT THEREFOR

The present invention relates to direct particle agglutination tests which have as their objective the determination of the presence or absence of antigens in body fluids, such as serum, urine, cerebrospinal fluid or the like, as an aid in the diagnosis of certain physiological or pathological conditions in humans and animals.

The detection of microbial antigens in body fluids can be useful in the rapid diagnosis of an increasing number of infections. However, a major problem is that currently available procedures are not sufficiently sensitive (immunodiffusion, CIE) and therefore fail to indicate the presence of antigens in a substantial proportion of infected patients or are too time consuming for rapid diagnosis (RIA, ELISA). In some instances, the antigen-antibody complex is slow to form and/or the particles formed are too small to be observed with certainty. Detectability has been improved by using agglutination tests employing particles as carriers on the surface of which the antigen or antibody molecule is adsorbed or bound.

Such agglutination testing may be performed by the indirect method, wherein the clinical sample is mixed with antibody at specified dilution, after an appropriate incubation period an indicator system consisting of a complex of the antigen bound to a particulate carrier is added to the mixture. If antigen is present in the clinical sample the antibody will not be available to react with the antigen-carrier complex and there will be no agglutination, thus, absence from agglutination is a positive test for the antigen. Conversely, if the antigen is not present in the clinical sample the antibody will react with the antigen-carrier complex causing agglutination of the indicator sample. The theory by which such agglutination tests work is well known in the art as illustrated in U.S. Pat. Nos. 3,171,783; 3,775,536; 3,873,683; 3,879,262; 4,003,988 and 4,045,384.

It has long been felt that the only truly meaningful diagnostic approach to the infectious disease area is early, rapid detection of antigens associated with the infectious agent, thus providing immediate direction for effective treatment.

This invention is concerned with a direct agglutination test for the detection of antigens.

In accordance with the present invention, an extremely sensitive agglutination test for the detection of antigens, such as proteins and the polysaccharides of various microorganisms including bacteria, protozoa and fungi in low concentrations in body fluids, has now been developed. A test according to the present invention is described which routinely detects as little as 0.2 nanograms per milliliter of the capsular polysaccharides associated with pathogenic bacteria. This represents a sensitivity 25 to 250 times greater than the widely used counter-current immunoelectrophoresis methods (CIE) and a sensitivity at least equal to radioimmunoassay (RIA). In addition, while CIE is rapid, it requires trained laboratory personnel and moderately expensive reagents and equipment and yields a limited sensitivity of 10 to 50 nanograms per ml. for most bacterial polysaccharides. Since lower concentrations of antigen frequently occur in body fluids, false negative CIE tests are often observed in patients with culture documented bacterial infections. RIA on the other hand is 10 to 100 fold more sensitive than CIE but is much more time consuming and expensive.

Prior to the present invention, the widespread use of particle agglutination tests, although extremely simple and inexpensive, has been limited due to the low degree of sensitivity of such tests to small concentrations of the antigen and poor specificity manifested by the occurrence of non-specific agglutination, particularly with serum specimens. By employing the methodology of the present invention as hereinafter set forth, a sensitivity of the order of 0.2 ng/ml is achieved and the frequency of non-specific agglutination with human sera is reduced to 2% or less. Further, a judicious choice and preparation of antiserum has produced a test characterized by uniform sensitivity, good stability and specificity.

It is therefore an object of this invention to provide a sensitive particle agglutination test for the detection of microbial antigens in body fluids at concentrations as low as 0.2 ng per milliliter of body fluid.

Another object is to provide a particle agglutination test characterized by a rate of non-specific agglutination with human sera of 2% or less.

It is particular object of the present invention to provide an improved particle agglutination assay for the rapid detection of polyribophosphate (PRP) the capsular polysaccharide of *Haemophilus Influenzae* Type b.

Limited sensitivity is the major problem with previously described methods for microbial antigen detection. As a consequence, bacterial antigen cannot be detected in all patients with documented infections. For example, tests have revealed that 7–22% of patients with H.i.b. meningitis; 38% with H.i.b. epiglottitis; 20–39% with bacteremic pneumococcal pneumonia and 50 to 90% with non-bacteremic pneumoccocal pneumonia fail to have detectable antigen in serum or cerebrospinal fluid when tested by available counter-current immunoelectrophoresis or particle agglutination assays. However, a radioimmunoassay capable of detecting 0.5 ng/ml or less will be able to diagnose virtually all cases of H.i.b. meningitis when they first present to the physician. The test results also indicate that the concentration of antigen in 37% of the patients was less than 10 ng/ml and therefore below the sensitivity of most available counter-current immunoelectrophoresis techniques.

In accordance with the present invention, a particle agglutination assay having a degree of sensitivity comparable to radioimmunoassay has been developed. The high degree of sensitivity achieved by the assay of the present invention results from modifications of previously known particle agglutination assays, namely, selection of a specific H.i.b. antiserum, use of a globulin fraction of the antiserum, washing the sensitized particle, and prolonging the incubation period of the particle agglutination assay from the usual 5 to about 45 minutes or longer.

a. Sensitivity

The choice of antiserum markedly affects the sensitivity of the assay. Six antisera prepared in three species of animals produces particles with sensitivities ranging from 0.2 nanograms to greater than 1000 nanograms PRP per milliliter. The functional quality of the specific antibody, as well as its concentration are important. The antiserum which produces the most sensitive particle does not have the highest concentration of antibody as determined by radioantigen binding assay.

Six antisera against whole *Haemophilus influenzae* Type b were prepared in four rabbits, a burro and a horse according to immunizing schedules described by H. E. Alexander et al in the Journal of Immunology 54: 207–211, 1946.

The term "particles" as used in connection with the present invention means particles which are inert and neutral towards the other components and which are able to adsorb antisera in an irreversable manner. Such particles may be glass beads, polybutadiene, polystyrene, polybutadiene-styrene, etc. having an average particle size of from about 0.15 to about 0.9 microns. Preferably polystyrene latex particles with a uniform diameter of approximately 0.81μ as a 10% wt/volume suspension in distilled water are sensitized with the foregoing antisera in the following manner:

The burro and rabbit whole antisera were each diluted 1/500 and the horse whole antiserum 1/200 in standard glycine buffered saline (0.1 M glycine, 0.9% sodium chloride, pH 8.2). Antibody was adsorbed on to latex particles by adding one part 10% latex suspension to 80 parts diluted antiserum, and incubated at room temperature for one hour. Free antiserum was decanted after centrifugation for 10 minutes at 12,000 G. The latex pellet was suspended in glycine buffered saline with a small amount of protein, i.e., 0.1% human serum albumin, or 0.1% burro, rabbit or horse serum as the case may be to make a 0.125% latex suspension re-centrifuged and resuspended in glycine buffered saline. Fetal calf serum, shown to have no anti-PRP antibody by radioimmunoassay, was used as a diluent for standard solutions of PRP antigen.

Agglutination was performed by adding 0.05 ml aliquots of antigen containing fluid to 0.01 ml sensitized latex solution on a serologic slide with ceramic rings. The slide was rotated (180 rpm) within a humidified chamber at ambient temperature and examined for agglutination after 45 minutes. Agglutination was graded 4+ when the agglutination mixture cleared, and coarse clumps of latex particles were observed, 3+ when the mixture remained cloudy but coarse clumps were observed, 2+ when the mixture remained cloudy but granularity was readily observed, and 1+ when the mixture remained cloudy but only minimal granularity was observed. Agglutination of 2+ or greater was considered positive. The comparative sensitivities are set forth in table 1.

TABLE 1

Sensitivity of LPA assay with six antisera to *Hemophilus Influenzae* Type b

| Serum | | Anti-PRP antibody[1] in whole serum (μg Ab protein/ml) | Anti-PRP antibody[1] absorbed to latex particles (μg Ab protein/ml LP) | Sensitivity[2] of LPA (ng PRP/ml) |
|---|---|---|---|---|
| Burro | | 11,200 | 3.40 | 0.2 |
| Rabbit | 1 | 96,000 | 7.84 | 1.0 |
| | 2 | 68,000 | 7.20 | 1.0 |
| | 3 | 45,000 | 6.56 | 5.0 |
| | 4 | 10,300 | 1.95 | 10.0 |
| Horse | | 3,100 | 1.84 | 1000 |

[1]Measured by Radioantigen binding assay.
[2]Lowest concentration of PRP-5 in fetal calf serum giving agglutination of 2+ or greater.

Table 1 clearly demonstrates that the quality of the antiserum used to sensitize the latex particles is critical to the sensitivity of the latex particle agglutination test for the detection of PRP antigen. In viewing the results set forth in Table 1 it is readily apparent that sensitivity cannot be predicted solely on the basis of the concentration of PRP in the antiserum as measured by the radioantigen binding assay. A burro antiserum, containing only 12% as much antibody as the best rabbit antiserum produced a 5-fold more sensitive latex particle preparation. This difference in sensitivity could not be explained by more effective coating of latex particles with burro antibody, since latex particles coated with rabbit antiserum had 2.3 times more absorbent antibody. The agglutination activity of burro and rabbit antiserum for sheep red blood cells coated with PRP was equal, despite the much higher concentration of PRP binding activity in the rabbit antiserum.

Measurement of association rates shows that burro antibody combines much more rapidly with PRP antigen than does rabbit antibody. The association half-life is 20 minutes for burro antibody and more than 60 minutes for rabbit antibody. The reason for this difference in association rate is unknown.

The dissocation rate of antigen-antibody complexes in the presence of excess antigen is a measure of the tightness of binding or affinity of the antibody. The rabbit antibody dissociates more slowly from polyribose-phosphate than did burro antibody and therefore has a greater affinity for antigen. This result lends support to the hypothesis that the rate of combination of antigen and antibody is more significant in agglutination processes than the strength of the antigen-antibody interaction.

b. Use of Macroglobulin Fraction to Coat LP

Molecular sieve chromatography of various animal antisera to bacterial polysaccharides revealed that the majority of the anti-polysaccharide antibody in the equine animals (burro, horse) is found in the macroglobulin class which elutes in the void volume of this column. In contrast, the majority of rabbit antibody is found in the IgG class which elutes later. As indicated in Table 2, the use of the macroglobulin fraction of burro or horse antiserum at a concentration of 50 μg protein/ml to sensitize latex particles may markedly improve the sensitivity of relatively weak equine antisera. The sensitivity of the best antisera is not further improved by this modification, although the clarity of the agglutination reaction is generally better with the void volume fraction. The use of the IgG fraction of rabbit sera does not produce comparable improvements in sensitivity or clarity of agglutination.

TABLE 2

Comparison of sensitivities of latex particles coated with whole serum or the macroglobulin fraction of equine antisera against bacterial polysaccharides

| Animal | Antiserum directed against | Sensitivity* of LP coated with whole serum (1/500 dilution) | Sensitivity of LP coated with macroglobulin fraction (50μg protein/ml) |
|---|---|---|---|
| Burro-F | H. influenzae type b | 1 ng/ml | 0.2 ng/ml |
| Burro-132 | H. influenzae type b | 0.2 ng/ml | 0.2 ng/ml |
| Burro-W.J. | H. influenzae type b | 2 ng/ml | 0.5 ng/ml |
| Burro-Y | Neisseria meningitidis-group Y | 1 ng/ml | 0.2 ng/ml |
| Horse-49 | N. meningitidis group A | 0.5 ng/ml | 0.2 ng/ml |
| Horse-46 | N. meningitidis group B | >10,000 ng/ml | 2 ng/ml |

*The lowest concentration of antigen producing 2+ agglutination or greater is indicated.

c. Washing of Coated LP

In order to effect further improvement in the sensitivity of the burro antisera, the antibody coated latex particles, coated with various dilutions of burro antiserum in glycine buffered saline, are compared unwashed and after one, two and three washings with glycine buffered saline containing 1/1000 parts fetal calf serum and the results reported in Table 3.

TABLE 3

Effect of dilution of antiserum and washing of latex particles on sensitivity of Latex Particle Agglutination Test for Polyribosephosphate

| Dilution of burro antiserum used to sensitize latex particles | Minimum concentration of PRP detected* (ng/ml) | | | |
|---|---|---|---|---|
| | Unwashed | Washed × 1 | Washed × 2 | Washed × 3 |
| 1/10 | 200 | >1000 | >1000 | >1000 |
| 1/100 | 50 | 0.5 | 0.5 | 0.5 |
| 1/500 | 2 | 0.2 | 0.2 | 0.2 |
| 1/1000 | 0.5 | 0.2 | 0.2 | 0.2 |
| 1/2000 | 0.2 | 0.2 | 0.2 | 0.5 |
| 1/5000 | >1000 | >1000 | >1000 | >1000 |

*2+ agglutination or greater was considered a positive result.

As can be seen from the results reported in Table 3, low dilutions of antiserum are insensitive. With dilutions of 1/500 and greater maximal sensitivity is attained provided the latex particles are washed. Unwashed latex particles attained maximal sensitivity with only a narrow range of dilutions. Two washes produced maximal sensitivity whereas three washes can result in diminished sensitivity.

Sensitized latex particles from the washing experiment were stored at 4° C. and retested after 12 and 24 months. Latex particles sensitized with 1/500 and 1/1000 dilution of burro antiserum and washed twice retained their original sensitivity whereas unwashed latex particles were two to four fold less sensitive after 24 months.

d. Duration of the Incubation Period

FIG. 1 of the drawings shows the relationship of assay sensitivity to incubation period. Large concentrations of antigen agglutinated the latex particles within five minutes. Sensitivity increased rapidly during the first 45 to 60 minutes and, slowly thereafter, reaching a maximum of 0.05 nanograms/ml with the most sensitive preparations at 10 hours. The equine serum of the present invention was more sensitive than rabbit serum at all incubation periods. In carrying out the comparative study fifty microliters of sample solution and ten microliters of coated latex particles, as hereinafter described, were mixed on a serological slide, and rotated at 180 revolutions/minute at room temperature. The slides were covered and humidity maintained with sponges saturated with hot water. The slides were viewed at the times indicated.

Prolonging the incubation period from five minutes to forty-five minutes or longer results in a 10 to 20-fold increase in sensitivity. For practical clinical purposes, an incubation period of 45 minutes normally read at 5-15 minute intervals was chosen when using latex particles coated with a equine antiserum. Such latex particles had a sensitivity of 0.2 nanograms antigen per milliliter of fluid.

It was anticipated that increasing the sensitivity of particle agglutination assays would also increase the incidence of non-specific agglutination, and indeed, in the case of serum specimens, 69% of sera from hospitalized children agglutinated these latex particles. This major drawback has previously limited the widespread use of this assay. Factors which have been implicated in the agglutination of latex particles coated with gamma globulins are heat labile serum components (presumably complement) and heat stable anti-globulins, low levels of which are commonly found in human sera particularly from patients with chronic inflammatory diseases.

Non-specific agglutination was recognized by the agglutination of control latex particles sensitized with whole non-immune animal serum. When macroglobulin coated latex particles are used, the control latex particles are coated with the macroglobulin fraction of non-immune serum.

In accordance with the present invention, the frequency of non-specific agglutination with human sera was reduced to 2% or lower by (i) the addition of non-immune animal serum to the sensitized latex particles; (ii) by the addition of a serum buffer containing a polyanion and/or a reducing agent directly to the incubation mixture and/or (iii) by heat inactivation of the sera.

The incidence of non-specific agglutination was determined with sera collected from hospitalized pediatric and adult patients who did not have H.i.b. disease. All sera were tested with latex particles sensitized with burro antiserum (anti-PRP LP) and with latex particles sensitized with non-immune burro serum (control LP).

In preliminary experiments, sera containing heat stable agglutinins were tested with the addition of 10 microliters of a reducing agent such as 1,4-dithiothreitol (DTT) or 2-mercapoethanol (ME) added to the incubation mixture at the beginning of incubation Optimal concentrations were 0.018 M for DTT and 0.35 M for ME (final concentrations in the incubation mixture were 0.0026 M for DTT and 0.05 M for ME).

Table 4 which follows summarizes the results obtained with 104 pediatric sera which had been stored at least 24 hours at 4° C. before testing.

TABLE 4

Incidence of non-specific agglutination with stored sera[1] from hospitalized children without *Haemophilus influenzae* type b disease

| Agglutination with Anti-PRP LP | Negative | Positive | Negative | Positive |
|---|---|---|---|---|
| Agglutination with Control LP | Negative | Positive | Positive | Negative |
| No treatment of serum (N = 104) | 32 (31%) | 65 (63%) | 3 (3%) | 4 (4%) |
| Heat inactivation of serum (n = 104) | 49 (47%) | 47 (45%) | 1 (1%) | 7 (7%) |
| Addition of normal burro serum (2.5%) to LP (n = 104) | 72 (69%) | 23 (22%) | 7 (7%) | 2 (2%) |
| Heat inactivation of serum and addition of normal burro serum (2.5%) to LP (n = 104) | 75 (72%) | 23 (22%) | 5 (5%) | 1 (1%) |
| Addition of normal burro serum (2.5%) to LP and addition of DTT[2] to serum (n = 53)[3] | 52 (98%) | 1 (2%) | 0 | 0 |

[1]Stored at least 24 hours at 4° C. before testing.
[2]Dithiothreitol, final concentration of 0.0026M in incubation mixture.
[3]Only 53 of 104 specimens contained sufficient serum for this test.

69% of the sera produced non-specific agglutination with anti-PRP and all but 4% were identified by control LP.

Heat inactivation (60° C. for 15 minutes) reduced non-specific agglutination only slightly, to 53%, and the addition of non-immune burro serum to both anti-PRP and control LP reduced non-specific agglutination to 31%; and the addition of 10 microliters of a reducing agent, i.e., dithiothreitol lowered the incidence of non-specific reactions to 2%. Results obtained with 52 stored adult sera were similar. Only one serum producing non-specific agglutination (positive with anti-PRP LP and control LP) when 2.5 normal burro serum was added to the latex particles and DTT was added to the incubation mixture.

In order to determine whether fresh sera produce a higher rate of non-specific agglutination, 100 sera from adults were collected and immediately placed on ice and assayed on the same day. Each serum was tested with and without reducing agent (ME) and with and without heat inactivation (60° C. for 5 minutes). Agglutination was tested with anti-PRP LP and control LP each containing 2.5% normal burro serum and corresponded in all cases. The patterns of agglutination are summarized in Table 5.

TABLE 5

Non-specific agglutination with fresh sera from 100 adults without *Haemophilus influenzae* type b disease[1]

| Pattern | No heat inactivation | | Heat inactivation | | No. of sera | Interpretation |
|---|---|---|---|---|---|---|
| | No ME | ME[2] | No ME | ME[2] | | |
| 1. | (−) | (−) | (−) | (−) | 43 | No antiglobulins No complement |
| 2. | (+) | (−) | (+) | (−) | 28 | Antiglobulins only |
| 3. | (+) | (+) | (−) | (−) | 4 | Complement only |
| 4. | (−) | (+) | (−) | (−) | 14 | Complement only ("reactivated" by ME) |
| 5. | (+) | (+) | (+) | (−) | 10 | Antiglobulins and complement |
| 6. | (−) | (−) | (−) | (+) | 1 | |
| No. of sera producing Non-specific Agglutination | 42 | 38 | 38 | 1 | | |

[1]All assays were performed with anti-PRP and control LP containing 2.5% normal burro serum. There was complete correspondence of results between anti-PRP and control LP.
[2]2-mercaptoethanol, final concentration 0.05M in incubation mixture.

42% of untreated sera (no heat no reducing agent) produced non-specific agglutination. When a reducing agent (ME) is added, 28 of the sera became negative (Pattern 2) indicating the presence of antiglobulins. 14 sera that had initially been negative became positive (Pattern 4) indicating that a heat labile agglutinin was reactivated by mercaptoethanol. The net effect of ME alone was to reduce non-specific agglutination to 38%. A similar rate of non-specific agglutination is achieved with heat inactivation alone. However, the combination of heat inactivation of the sera and the addition of a reducing agent to the incubation mixture reduced the incidence of non-specific agglutination to the order of 2% or lower.

Because heat inactivation is time consuming, an alternative method to eliminate non-specific agglutination by heat labile serum factors has been developed. A variety of polyanions including sodium polyanethol sulfonate (SPS), dextransulfate, carrageenin and heparin prevent the non-specific agglutination of globulin-coated latex particles by heat labile serum factors.

One hundred fresh sera from adults were tested with a serum buffer containing both ME (as above) and SPS at a concentration of 0.05%. Only one of the 100 sera produced non-specific agglutination with anti-PRP and control LP. Non-specific agglutination with this serum was eliminated by heating.

Desirably, a serum buffer comprising both reducing agent and a polyanion is added to the incubation mixture of a stabilized sensitized latex particle and a serum specimen.

Such a serum buffer is prepared as follows:

Dilute 14 molar 2-mercaptoethanol (standard full-strength solution) 1/40 in glycine buffered saline (GBS) (0.1 M glycine, 0.9% sodium chloride, pH 8.2). Dilute 5% aqueous solution of polyanethol sulfonate 1/100 in same GBS.

The serum buffer may contain other reducing agents such as dithiothreitol, glutathione, cysteine and the like in lieu of 2-mercaptoethanol. In addition, other polyanions such as dextran sulfate, heparin and carrageenin and the like may be used so long as they do not interfere with the antigen-antibody reaction.

Table 6 which follows, shows the optimal concentration of reagents in the serum buffer. Higher concentrations of reducing agents or polyanions reduced the sensitivity of the assay and lower concentrations failed to eliminate non-specific agglutination in all sera.

TABLE 6

Optimal concentrations of reagents in "serum buffer"

| | DTT | 2-ME | SPS |
|---|---|---|---|
| | (final concentrations in assay mixture) | | |
| Decreased sensitivity | 12.8 mM | 400 mM | 0.07% |
| Good sensitivity + elimination of non-specific agglutination | 2.6 mM | 50 mM | 0.007% |
| Failure to eliminate non-specific agglutination | 0.65 mM | 10 mM | 0.0007% |

DTT - dithiothreitol
2-ME 2-mercaptoethanol
SPS - sodium polyanethosulfonate

The effective concentration of non-immune animal serum in the latex suspension was reexamined in the test system using the serum buffer described above.

Concentrations of non-immune animal serum of less than 0.25% in the particle suspension (less than 0.035% in the final assay mixture) resulted in occasional non-specific agglutination despite the use of serum buffer.

Concentrations of non-immune animal serum up to about 25% in the latex suspension (3.5% in the final assay mixture) are effective in reducing the incidence of non-specific agglutination, however, the highest concentration, i.e., 25% reduced the sensitivity of the assay for polyribophosphate two-fold.

Non-Specific Agglutination in Other Body Fluids

Most urine specimens produce non-specific agglutination with anti-PRP and control LP. This can be eliminated either by heating (100° C. for 5 minutes) or by filtering the urine. In the preferred embodiment a 0.45 micron filter is used.

Cerebrospinal fluid specimens very rarely produce non-specific agglutination which is eliminated by heating (100° C. for 5 minutes). The PRP antigen is stable to the above heating and filtration procedures.

The following specific example demonstrates the invention in its preferred embodiment.

a. Coating of latex particles

To make anti-PRP latex particles, whole burro antiserum to *H. influenzae* type b is diluted 1/500 in glycine buffered saline (GBS) and heated to 56° C. for 30 minutes. One part latex suspension (a 10% suspension of 0.81μ diameter particles in distilled water) is added to 80 parts diluted antiserum for a final latex particle concentration of 0.125%. The mixture is incubated for 1 hour at room temperature, centrifuged at 12,000 G for 10 minutes, and the supernatant discarded. The pellet is resuspended in an equal volume of GBS containing 0.1% non-immune burro serum, recentrifuged as above and then resuspended in an equal volume of GBS containing 2.5% non-immune burro serum. Control latex particles are prepared as above except that non-immune burro serum diluted 1/500 in GBS is used to initially coat the latex particles. The non-immune burro serum used throughout should be serum taken prior to immunization from the same animal that was immunized.

When the macroglobulin fraction is to be used, the whole pre-immune and immune burro serum are chromatographed on a Sephacryl G-200 gel filtration column and the fractions eluting in the void volume of the column are pooled. The pooled void volume fractions, diluted to a protein concentration of 50 μg protein per milliliter in GBS, are then substituted for diluted whole serum in the method described above.

b. Preparation of Serum Buffer

Dilute 14 molar 2-mercaptoethanol (standard full strength solution) 1/40 in GBS. Add sodium polyanethol sulfonate to a final concentration of 0.05%.

c. Assay Procedure

The assay procedure carried out in accordance with the present invention is as follows:

50 microliters of positive control serum, negative control serum and each serum, cerebrospinal fluid and urine specimen to be tested is added to each of two wells of a clean dry serologic slide per the following diagram. The positive control serum contains 2 ng PRP antigen/ml. The negative control serum contains antiglobulins which agglutinate both anti-PRP LP and control LP unless SB is added, thus providing a check on the activity of the SB. Urine specimens are pre-filtered with a 0.45 micron filter.

|                  | Positive Control Serum | Negative Control Serum | Test Serum | Test CSF | Test Urine |
|------------------|:----------------------:|:----------------------:|:----------:|:--------:|:----------:|
| Row A: Anti-PRP LP | SB | SB | SB | ○ | ○ |
| Row B: Control LP  | SB | SB | SB | ○ | ○ |

Add 10 microliters of serum buffer to each well containing positive control serum, negative control serum or a serum specimen.

The latex suspensions are gently mixed without foaming and 10 microliters of anti-PRP latex particles are added to one well of each pair (Row A) and the reagents mixed throughly.

10 microliters of control latex particles are added to the second well of each pair and the reagents are mixed throughly.

The slide is placed on a serologic shaker and rotated for approximately 45 minutes. The chamber should be humidified by sponges soaked in hot water with condensation being visible throughout the run. The slide is removed from the chamber, wiped free of condensation and agglutination is read while tilting back and forth in oblique light over black background as follows:

4+ large clumps—clear background
3+ large clumps—milky background
2+ small clumps
1+ finely granular
0 milky 3+ and 4+ reactions should be readily distinguishable from controls when viewing the slide at arm's length. 2+ reactions require closer inspection.

Interpretation of results.

| Hemophilus LP | Control LP | Interpretation |
|:---:|:---:|---|
| (+) | (−) | Positive for *H. influenzae* type b antigen. |
| (−) | (−) | Negative for '*H. influenzae* type b antigen. |
| (+) | (+) | Non-specific agglutination. *H. influenzae* type b antigen may or may not be present. |

Positive agglutination of 2+ should be reported as "weakly positive."

As used throughout the specification time durations and temperatures employed during heat treatment and incubation are optimal it being understood that the same results may be obtained at higher temperatures for shorter time period or conversely lower temperatures for longer time periods. Further, the foregoing specification discloses reagents, media and techniques used in establishing the operability of the present invention. It will be readily evident, however, to those skilled in the art that variations in techniques, times, volumes and types of materials, media and equipment can be used without departing from the scope of the present invention, which is limited only by the scope of the appended claims.

What is claimed is:

1. A reagent for the detection of antigens in body fluids suspected of containing such antigens as well as heat labile and heat stable agglutinins, which comprises a suspension of finely divided particles having absorbed thereon antibody against such antigens and a buffer system including a mixture of a polyanion capable of minimizing the effects of heat labile agglutinins in the body fluid and a reducing agent capable of minimizing the effects of heat stable agglutinins in the body fluid.

2. The reagent of claim 1 wherein the polyanion is selected from the group consisting of sodium polyanethol sulfonate, dextran sulfate, carrageenin and heparin.

3. The reagent of claim 1 wherein the reducing agent is selected from the group consisting of 2-mercaptoethanol, dithiothreitol, glutathione and cysteine.

4. The reagent of claim 1 which includes non-immune animal serum or the gamma globulin fraction thereof.

5. In a direct agglutination method for the detection of antigens in body fluids suspected of containing such antigens as well as heat labile and heat stable agglutinins, which method comprises preparing a reaction mixture by mixing a specimen of such body fluid with a liquid reagent comprising carrier particles coated with animal antiserum or an immunoglobulin fraction thereof against such antigens suspended in a compatible physiological buffering system, the improvement which comprises adding to the reaction mixture a buffer system which includes a polyanion capable of minimizing the effects of heat labile agglutinins in the specimen and a reducing agent capable of minimizing the effects of heat stable agglutinins in the specimen and which permits recognition of a positive specific reaction with the antigen and avoids a positive non-specific reaction.

6. The method of claim 5 wherein said polyanion is selected from the group consisting of sodium polyanethol sulfonate, dextran sulfate, carrageenin and heparin.

7. The method of claim 5 wherein said reducing agent is selected from the group consisting of 2-mercaptoethanol, dithiothreitol, glutathione and cysteine.

8. The method of claim 5 wherein the body fluid is serum.

9. The method of claim 5 wherein the body fluid is plasma.

10. The method of claim 5 wherein non-immune animal serum or the gamma globulin fraction thereof is included in the reaction mixture.

11. A method for detecting polyribophosphate (PRP) in a specimen of body fluid suspected of containing the same as well as heat labile and heat stable agglutinins which comprises forming a reaction mixture by mixing reagent comprising an aqueous suspension of finely divided particles having absorbed thereon antibody specific to PRP, said antibody being derived from an equine species immunized with PRP, with a specimen of said body fluid and a buffer system including a polyanion and a reducing agent capable of minimizing the effects of heat labile and heat stable agglutinins respectively, incubating said reaction mixture and thereafter determining the presence of agglutination, the presence of agglutination indicating the presence of PRP in the specimen of body fluid.

12. The method of claim 11 wherein there is further included in said reaction mixture a normal equine serum which does not contain antibody specific to PRP.

13. The method of claim 11 wherein said polyanion is selected from the group consisting of sodium polyanethol sulfonate, dextran sulfate, carrageenin and heparin.

14. The method of claim 11 wherein said reducing agent is selected from the group consisting of 2-mercaptoethanol, dithiothreitol, glutathione and cysteine.

* * * * *